(12) United States Patent
Hijikata et al.

(10) Patent No.: US 6,783,935 B2
(45) Date of Patent: Aug. 31, 2004

(54) GENETIC POLYMORPHISM OF MXA PROTEIN AND USE THEREOF

(75) Inventors: Minako Hijikata, Minato-Ku (JP); Shunji Mishiro, Minato-Ku (JP); Yasuhiko Oota, Minato-Ku (JP); Koji Hashimoto, Minato-Ku (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 30 days.

(21) Appl. No.: 09/813,990

(22) Filed: Mar. 22, 2001

(65) Prior Publication Data

US 2002/0127558 A1 Sep. 12, 2002

(30) Foreign Application Priority Data

Mar. 22, 2000 (JP) ........................................ 2000-080955
Mar. 6, 2001 (JP) ........................................ 2001-062371

(51) Int. Cl.[7] .................. C12Q 1/68; C12N 15/00; C12N 15/63; C12N 1/20; C07H 21/04
(52) U.S. Cl. .................. 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search ....................... 435/6, 91.1, 91.2, 435/70.1, 320.1; 536/24.3, 23.4, 22.1, 24.1, 24.2; 935/6; 436/518; 530/350

(56) References Cited

U.S. PATENT DOCUMENTS 5,776,672 A  7/1998  Hashimoto et al. ............ 435/6
5,972,692 A  10/1999  Hashimoto et al.

OTHER PUBLICATIONS

Krol et al., "Identification of genes in Rhizobium Leguminosarum bv. trifolii whose products are homologues to a family of ATP–binding proteins", Microbiology, (1997), vol. 143, pp. 1389–1394.*

Cross et al., "Purification of cPG islands using a methylated DNA binding column", Nature Genetics, (1994), vol. 6, pp. 236–244.*

E. Masson, et al., Pharmachokinetic Optimisation of Cancer Chemotherapy, Disease Manangement, 1997, pp. 325–343.*

Guido Antonelli, et al.; "Correlation of Interferon–Induced Expression of MxA mRNA in Peripheral Blood Mononuclear Cells With the Response of Patients With Chronic Active Hepatitis C to IFN–α Therapy", Journal of Interferon and Cytokine Research vol. 19; (1999); pp. 243–251.

Tapani Ronni, et al.; "The Proximal Interferon–Stimulated Response Elements are Essential for Interferon Responsiveness: A Promoter Analysis of the Antiviral MxA Gene"; Journal of Interferon and Cytokine Research vol. 18, (1998) pp. 773–781.

K. C. Chang, et al.; "Molecular and Functional Analysis of the Virus– and Interferon–Inducible Human MxA Promoter"; Archives of Virology (1991); pp. 1–15.

U.S. patent application Ser. No. 10/633,659, Hijikata et al., filed Aug. 5, 2003.

U.S. patent application Ser. No. 09/813,990, Hijikata et al., filed Mar. 22, 2001.

U.S. patent application Ser. No. 5,776,672, Hashimoto et al., filed Jul. 7, 1998.

U.S. patent application Ser. No. 09/813,990, filed Mar. 22, 2001, pending.

U.S. patent application Ser. No. 10/070,415, filed Mar. 15, 2002, pending.

\* cited by examiner

Primary Examiner—Jeffrey Fredman
Assistant Examiner—Arun Chakrabarti
(74) Attorney, Agent, or Firm—Oblon, Spivak, McClelland, Maier & Neustadt, P.C.

(57) ABSTRACT

The present invention provides polynucleotides having base sequences of sequence Nos. 1 to 4, as polynucleotides having polymorphism sites capable of being useful indicators for prediction of validity of interferon therapy.

9 Claims, 5 Drawing Sheets

SEQUENCE LISTING

<160> NUMBER OF SEQ ID NOS: 23

<210> SEQ ID NO 1
<211> LENGTH: 581
<212> TYPE: DNA
<213> ORGANISM: Homo sapiens

<400> SEQUENCE: 1

```
atgagccaga ctccagggag gcctagaagt gggcaagggg aaacgggaaa ggaggaagat      60
ggtatgggtg tgcctggtta ggggtgggag tgctggacgg agttcgggac aagagggggct    120 ctgcagccat tggcacacaa tgcctgggag tccctgctgg tgctgggatc atcccagtga    180
gccctgggag ggaactgaag accccccaatt accaatgcat ctgttttcaa aaccgacggg    240
gggaaggaca tgcctaggtt caaggatacg tgcaggcttg gatgactccg ggccattagg    300
gagcctccgg agcaccttga tcctcagacg ggcctgatga aacgagcatc tgattcagca    360
ggcctgggtt cgggcccgag aacctgcgtc tcccgcgagt tcccgcgagg caagtgctgm    420
aggtgcgggg ccaggagcta ggtttcgttt ctgctcccgg agccgccctc agcacagggt    480
ctgtgagttt catttcttcg ccggcgcggg gcggggctgg gcgcggggtg aaagaggcga    540
accgagagcg gaggccgcac tccagcactg cgcagggacc g                         581
```

<210> SEQ ID NO 2
<211> LENGTH: 581
<212> TYPE: DNA
<213> ORGANISM: Homo sapiens

<400> SEQUENCE: 2

```
atgagccaga ctccagggag gcctagaagt gggcaagggg aaacgggaaa ggaggaagat      60
ggtatgggtg tgcctggtta ggggtgggag tgctggacgg agttcgggac aagagggget     120
ctgcagccat tggcacacaa tgcctgggag tccctgctgg tgctgggatc atcccagtga     180
gccctgggag ggaactgaag accccccaatt accaatgcat ctgttttcaa aaccgacggg    240
gggaaggaca tgcctaggtt caaggatacg tgcaggcttg gatgactccg ggccattagg     300
gagcctccgg agcaccttga tcctcagacg ggcctgatga aacgagcatc tgattcagca     360
ggcctgggtt cgggcccgag aacctgcgtc tcccgcgagt tcccgcgagg caagtgctgm     420
aggtgcgggg ccaggagcta ggtttcgttt ctgcgcccgg agccgccctc agcacagggt     480
ctgtgagttt catttcttcg ccggcgcggg gcggggctgg gcgcggggtg aaagaggcga     540
accgagagcg gaggccgcac tccagcactg cgcagggacc g                         581
```

<210> SEQ ID NO 3
<211> LENGTH: 581
<212> TYPE: DNA
<213> ORGANISM: Homo sapiens

<400> SEQUENCE: 3

```
atgagccaga ctccagggag gcctagaagt gggcaagggg aaacgggaaa ggaggaagat      60
ggtatgggtg tgcctggtta ggggtgggag tgctggacgg agttcgggac aagagggget     120
ctgcagccat tggcacacaa tgcctgggag tccctgctgg tgctgggatc atcccagtga     180
gccctgggag ggaactgaag accccccaatt accaatgcat ctgttttcaa aaccgacggg    240
gggaaggaca tgcctaggtt caaggatacg tgcaggcttg gatgactccg ggccattagg     300
gagcctccgg agcaccttga tcctcagacg ggcctgatga aacgagcatc tgattcagca     360
ggcctgggtt cgggcccgag aacctgcgtc tcccgcgagt tcccgcgagg caagtgctgm     420
aggtgcgggg ccaggagcta ggtttcgttt ctgcacccgg agccgccctc agcacagggt     480
ctgtgagttt catttcttcg ccggcgcggg gcggggctgg gcgcggggtg aaagaggcga     540
accgagagcg gaggccgcac tccagcactg cgcagggacc g                         581
```

<210> SEQ ID NO 4
<211> LENGTH: 581
<212> TYPE: DNA
<213> ORGANISM: Homo sapiens

<400> SEQUENCE: 4

```
atgagccaga ctccagggag gcctagaagt gggcaagggg aaacgggaaa ggaggaagat      60
ggtatgggtg tgcctggtta ggggtgggag tgctggacgg agttcgggac aagagggget     120
ctgcagccat tggcacacaa tgcctgggag tccctgctgg tgctgggatc atcccagtga     180
gccctgggag ggaactgaag accccccaatt accaatgcat ctgttttcaa aaccgacggg    240
gggaaggaca tgcctaggtt caaggatacg tgcaggcttg gatgactccg ggccattagg     300
gagcctccgg agcaccttga tcctcagacg ggcctgatga aacgagcatc tgattcagca     360
ggcctgggtt cgggcccgag aacctgcgtc tcccgcgagt tcccgcgagg caagtgctgm     420
aggtgcgggg ccaggagcta ggtttcgttt ctgccccegg agccgccctc agcacagggt     480
```

-continued

```
ctgtgagttt catttcttcg ccggcgcggg gcggggctgg gcgcgggtg aaagaggcga      540 accgagagcg gaggccgcac tccagcactg cgcagggacc g                        581
```

<210> SEQ ID NO 5
<211> LENGTH: 16
<212> TYPE: DNA
<213> ORGANISM: Homo sapiens

<400> SEQUENCE: 5

```
ggtttcgttt ctgctc                                                    16
```

<210> SEQ ID NO 6
<211> LENGTH: 16
<212> TYPE: DNA
<213> ORGANISM: Homo sapiens

<400> SEQUENCE: 6

```
ggtttcgttt ctgcgc                                                    16
```

<210> SEQ ID NO 7
<211> LENGTH: 16
<212> TYPE: DNA
<213> ORGANISM: Homo sapiens

<400> SEQUENCE: 7

```
ggtttcgttt ctgcac                                                    16
```

<210> SEQ ID NO 8
<211> LENGTH: 16
<212> TYPE: DNA
<213> ORGANISM: Homo sapiens

<400> SEQUENCE: 8

```
ggtttcgttt ctgccc                                                    16
```

<210> SEQ ID NO 9
<211> LENGTH: 11
<212> TYPE: DNA
<213> ORGANISM: Homo sapiens

<400> SEQUENCE: 9

```
ttctgctccc g                                                         11
```

<210> SEQ ID NO 10
<211> LENGTH: 11
<212> TYPE: DNA
<213> ORGANISM: Homo sapiens

<400> SEQUENCE: 10

```
ttctgcgccc g                                                         11
```

<210> SEQ ID NO 11
<211> LENGTH: 11
<212> TYPE: DNA
<213> ORGANISM: Homo sapiens

<400> SEQUENCE: 11

```
ttctgcaccc g                                                         11
```

<210> SEQ ID NO 12
<211> LENGTH: 11
<212> TYPE: DNA
<213> ORGANISM: Homo sapiens

```
<400> SEQUENCE: 12
ttctgccccc g                                                          11

<210> SEQ ID NO 13
<211> LENGTH: 16
<212> TYPE: DNA
<213> ORGANISM: Homo sapiens

<400> SEQUENCE: 13
gagcagaaac gaaacc                                                     16

<210> SEQ ID NO 14
<211> LENGTH: 16
<212> TYPE: DNA
<213> ORGANISM: Homo sapiens

<400> SEQUENCE: 14
gcgcagaaac gaaacc                                                     16

<210> SEQ ID NO 15
<211> LENGTH: 16
<212> TYPE: DNA
<213> ORGANISM: Homo sapiens

<400> SEQUENCE: 15
gtgcagaaac gaaacc                                                     16

<210> SEQ ID NO 16
<211> LENGTH: 16
<212> TYPE: DNA
<213> ORGANISM: Homo sapiens

<400> SEQUENCE: 16
gggcagaaac gaaacc                                                     16

<210> SEQ ID NO 17
<211> LENGTH: 11
<212> TYPE: DNA
<213> ORGANISM: Homo sapiens

<400> SEQUENCE: 17
cgggagcaga a                                                          11

<210> SEQ ID NO 18
<211> LENGTH: 11
<212> TYPE: DNA
<213> ORGANISM: Homo sapiens

<400> SEQUENCE: 18
cgggcgcaga a                                                          11

<210> SEQ ID NO 19
<211> LENGTH: 11
<212> TYPE: DNA
<213> ORGANISM: Homo sapiens

<400> SEQUENCE: 19
cgggtgcaga a                                                          11

<210> SEQ ID NO 20
<211> LENGTH: 11
<212> TYPE: DNA
```

```
<213> ORGANISM: Homo sapiens

<400> SEQUENCE: 20
cgggggcaga a                                                         11

<210> SEQ ID NO 21
<211> LENGTH: 30
<212> TYPE: DNA
<213> ORGANISM: Homo sapiens

<400> SEQUENCE: 21
acacacccgt ttccaccctg gagaggccag                                     30

<210> SEQ ID NO 22
<211> LENGTH: 30
<212> TYPE: DNA
<213> ORGANISM: Homo sapiens

<400> SEQUENCE: 22
tgcgcagtgc tggagtgcgg cctccgctct                                     30

<210> SEQ ID NO 23
<211> LENGTH: 150
<212> TYPE: DNA
<213> ORGANISM: Homo sapiens

<400> SEQUENCE: 23
gtgcggggcc aggagctagg tttcgtttct gcgcccggag ccgccctcag cacagggtct    60
gtgagtttca tttcttcgcc ggcgcgggcg gggctggggc gcggggtgaa agaggcgaac   120
gagacggagg ccgcactcca gcactgcgca                                    150
```

GENETIC POLYMORPHISM OF MXA PROTEIN AND USE THEREOF

CROSS-REFERENCE TO RELATED APPLICATIONS

This application is based upon and claims the benefit of priority from the prior Japanese Patent Applications No. 2000-080955, filed Mar. 22, 2000; and No. 2001-062371, filed Mar. 6, 2001, the entire contents of both of which are incorporated herein by reference.

BACKGROUND OF THE INVENTION

The present invention relates to genetic polymorphism of MxA proteins and a method for predicting validity of interferon in an individual to be subjected to interferon therapy by using the genetic polymorphism.

Interferon is a protein secreted by vertebrate cells having antiviral activity, immunity control activity, and cell proliferation suppression activity. Therefore, interferon is widely used for treatment of various viral infectious diseases such as hepatitis C as well as malignant tumors. However, patients who do not exhibit sensitivity toward interferon have come to be known. Continuation of interferon therapy on such patients exhibiting no sensitivity to interferon therapy results in not only side effect such as fever and anemia, but also delay of initiating other treatments. Therefore, it is desirable to predict validity of interferon therapy to exclude such insensitive patients from interferon therapy, in advance.

On the other hand, an interferon-dependent protein, i.e, MxA proteins, having resistance against influenza viruses has been discovered from mice, and MxA protein has also been found in humans. In addition, it has been recently reported that expression levels of MxA mRNA and MxA proteins in patients who are infected with chronic hepatitis C virus (to be called HCV hereafter) are involved in responses of infected patients to interferon therapy. This fact suggests that MxA genes can be a useful indicator for prediction of validity of interferon therapy prior to application of the therapy.

Therefore, the present inventors examined the existence of genetic polymorphism in the MxA gene which is involved in response of HCV-infected patients to interferon therapy. The result showed that only the patients having specific genetic polymorphism of the MxA gene have sensitivity to interferon, and interferon therapy is valid to them.

BRIEF SUMMARY OF THE INVENTION

In view of the circumstances mentioned above, the first object of the present invention is to provide genetic polymorphism in the promoter region of MxA gene useful in predictiong validity of interferon therapy for patients.

The second object of the present invention is to provide a method for predicting validity of interferon therapy for patients using the genetic polymorphism in the promoter region of MxA gene described above.

The third object of the present invention is to provide gene therapy and a useful vector, for rendering interferon-insensitive patients to be interferon-sensitive, using a gene of particular genetic polymorphism of the MXA genes that is responsible for interferon-sensitivity.

According to the first aspect of the present invention, there is provided a polynucleotide for predicting validity of interferon therapy, which comprises a polynucleotide selected from the group consisting of:

(at) the polynucleotide of Sequence ID No. 1 in the sequence listing;

(bt) a modified polynucleotide derived from the polynucleotide (at) by including one or several deletions, substitutions or additions at any positions except for 455th position;

(ct) a polynucleotide containing the sequence which spans from 441st to 455th position of Sequence ID No. 1;

(dt) a polynucleotide containing the sequence which spans from 449the to 459th position of Sequence ID No. 1; and (et) a complementary strand of the polynucleotide selected from the group consisting of (at), (bt), (ct) and (dt) mentioned above.

According to the second aspect of the present invention, there is provided a polynucleotide for predicting validity of interferon therapy, which comprises a polynucleotide selected from the group consisting of:

(ag) the polynucleotide of Sequence ID No. 2 in the sequence listing;

(bg) a modified polynucleotide derived from the polynucleotide (ag) by including one or several deletions, substitutions or additions at any positions except for 455th position;

(cg) a polynucleotide containing the sequence which spans from 441st to 455th position of Sequence ID No. 2;

(dg) a polynucleotide containing the sequence which spans from 449th to 459th position of Sequence ID No. 2; and (eg) a complementary strand of the poly nucleotide selected from the group consisting of (ag), (bg), (cg) and (dg) mentioned above.

According to the third aspect of the present invention, there is provided a polynucleotide for predicting validity of interferon therapy, which comprises a polynucleotide selected from the group consisting of:

(aa) the polynucleotide of Sequence ID No. 3 in the sequence listing;

(ba) a modified polynucleotide derived from the polynucleotide (aa) by including one or several deletions, substitutions or additions at any positions except for 455th position;

(ca) a polynucleotide containing the sequence which spans from 441st to 455th position of Sequence ID No. 3;

(da) a polynucleotide containing the sequence which spans from 449th to 459th position of Sequence ID No. 3; and (ea) a complementary strand of the polynucleotide selected from the group consisting of (aa), (ba), (ca) and (da) mentioned above.

According to the fourth aspect of the present invention, there is provided a polynucleotide for predicting validity of interferon therapy, which comprises a polynucleotide selected from the group consisting of:

(ac) the polynucleotide of Sequence ID No. 4 in the sequence listing;

(bc) a modified polynucleotide derived from the polynucleotide (ac) by including one or several deletions, substitutions or additions at any positions except for 455th position;

(cc) a polynucleotide containing the sequence which spans from 441st to 455th position of Sequence ID No. 4;

(dc) a polynucleotide containing the sequence which spans from 449th to 459th position of Sequence ID No. 4; and (ec) a complementary strand of the polynucleotide selected from the group consisting of (ac), (bc), (cc) and (dc) mentioned above.

According to the fifth aspect of the present invention, there is provided a method of predicting whether interferon therapy is valid or not for an individual requiring interferon administration, comprising the steps of 1) taking a sample containing a polynucleotide which includes at least one interferon-stimulated response element from the individual; and 2) determining nucleotide located at the 2nd position from the 3' end of the at least one interferon-stimulated response element.

In the method, it can be predicted that interferon therapy is valid for the individual when the nucleotide is thymine. On the other hand, when the nucleotide is guanine, adenine, or cytosine, it can be predicted that interferon therapy is highly possibly invalid for the individual.

According to the sixth aspect of the present invention, there is provided a test reagent for predicting whether interferon therapy is valid or not for an individual requiring interferon therapy, which comprises a polynucleotide selected from the group consisting of (at) to (et), (ag) to (eg), (aa) to (ea), and (ac) to (ea) described above.

According to the seventh aspect of the present invention, there is provided a probe for detecting polymorphism existing in a promoter region of MxA gene, comprising a polynucleotide selected from the group consisting of (at) to (et), (ag) to (eg), (aa) to (ea), and (ac) to (ea) described above.

According to the eighth aspect of the present invention, there is provided use of the a polynucleotide selected from the group consisting of (at) to (et), (ag) to (eg), (aa) to (ea), and (ac) to (ea) described above, for predicting validity of interferon.

According to the ninth aspect of the present invention, there is provided a vector for rendering an interferon-insensitive individual to be interferon-sensitive, which contains at least one polynucleotide selected from the group consisting of the polynucleotides (at), (bt), (ct), (dt) and (et) described above.

According to the tenth aspect of the present invention, there is provided a method for rendering an interferon-insensitive individual to be interferon-sensitive, which comprises introducing a polynucleotide containing at least one polynucleotide selected from the group consisting of the polynucleotides (at), (bt), (ct), (dt) and (et) described above into the interferon-insensitive individual.

According to the eleventh aspect of the present invention, there is provided use of a polynucleotide which contains at least one polynucleotide selected from the group consisting of the polynucleotides (at), (bt), (ct), (dt) and (et) described above, in the production of pharmaceuticals for rendering an interferon-insensitive individual to be interferon-sensitive.

According to the twelfth aspect of the present invention, there is provided a non-human transgenic animal, which has been introduced with a polynucleotide which contains at least one polynucleotide selected from the group consisting of the polynucleotides (at), (bt), (ct), (dt) and (et) described above.

DETAILED DESCRIPTION OF THE INVENTION

Figure 1:
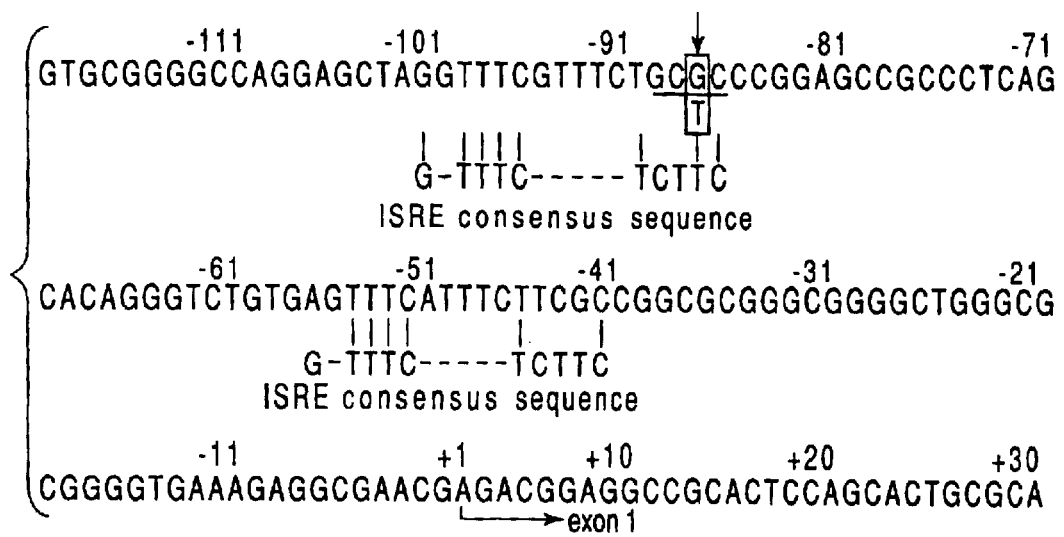
FIG. 1 shows the nucleotide sequence of promoter region of the MxA gene.
Figure 2:
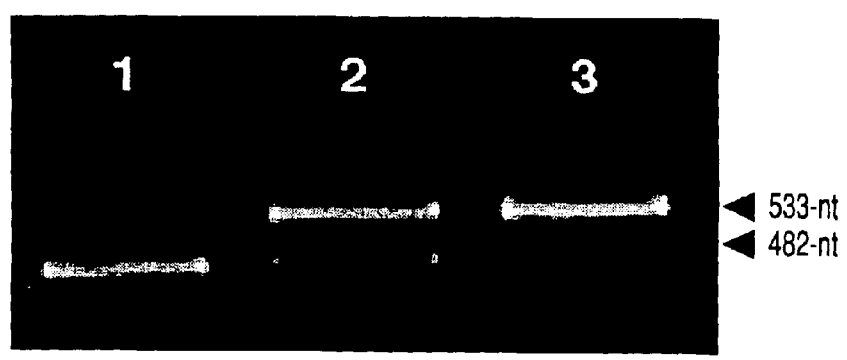
FIG. 2 shows the result of RFLP electrophoresis using HhaI.

Polynucleotides of Sequence ID Nos. 1, 2, 3 and 4 are those containing promoter regions of human MxA genes, and it was found for the first time by the present inventors that the single nucleotide polymorphism (to be called SNP hereafter) existing at 455th position of these polynucleotides contributes to responsibility to the effect of interferon therapy.

The interferon-stimulated response element (to be called ISRE hereafter) exists from 441st to 456th position of each polynucleotide.

The nucleotide sequence of ISRE from 441st to 456th position of Sequence ID No. 1 is [GGTTTCGTTTCTGCTC] (Sequence ID No. 5). The 15th position of ISRE (corresponding to 455th position of Sequence ID No. 1) is thymine. Note that according to the ordinary representation in which the transcription initiation site is referred to as +1st position, 455th position in Sequence ID No. 1 is designated as −88th position.

The nucleotide sequence of ISRE from 441st to 456th position of Sequence ID No. 2 is [GGTTTCGTTTCTGCGC] (Sequence ID No. 6). The 15th position of ISRE (corresponding to 455th position of Sequence ID No. 1) is guanine. Note that according to the ordinary representation in which the transcription initiation site is referred to as +1st position, 455th position in Sequence ID No. 1 is designated as −88th position.

The nucleotide sequence of ISRE from 441st to 456th position of Sequence ID No. 3 is [GGTTTCGTTTCTGCGC] (Sequence ID No. 7) and the 15th position of ISRE (corresponding to 455th position of Sequence ID No. 3) is adenine. Note that according to the ordinary representation in which the transcription initiation site is referred to as +1st position, 455th position in Sequence ID No. 3 is designated as −88th position.

The nucleotide sequence of ISRE from 441st to 456th position of Sequence ID No. 4 is [GGTTTCGTTTCTGCCC] (Sequence ID No. 8) and the 15th position of ISRE (corresponding to 455th position of Sequence ID No. 4) is cytosine. Note that according to the ordinary representation in which the transcription initiation site is referred to as +1st position, 455th position in Sequence ID No. 4 is designated as −88th position.

Hereinafter throughout the present specification, 455th position of Sequence ID Nos. 1, 2, 3, and 4 are called the SNP site.

The regions of these ISRE except for said SNP sites are common for each sequence. It was epidemiologically proved that while interferon therapy is effective for HCV-infected patients having ISRE (Sequence ID No. 5) in which the 15th nucleotide is thymine, interferon therapy is not effective for HCV-infected patients not having ISRE (Sequence ID No. 5) in which the 15th nucleotide is thymine.

In other words, as described in detail in examples described later, it was proved that interferon therapy is less effective for HCV-infected patients possessing homozygous promoter region comprising the polynucleotide of Sequence ID No. 2 which has guanine at 455th position (to be referred to G/G homo hereinafter), in comparison with those possessing heterozygous promoter regions comprising the polynucleotide of Sequence ID No. 1 which has thymine at the 455th position and the polynucleotide of Sequence ID No. 2 which has guanine at the 455th position (to be referred to G/T hetero hereinafter), or those having homozygous promoter region comprising the polynucleotide of Sequence ID No. 1 (to be referred to T/T homo hereinafter).

Alternatively, the interferon therapy was shown to be less effective for HCV-infected patients having homozygous promoter regions of MxA genes which has not thymine at the 455th position (to be referred to non-T/non-T homo hereinafter), in comparison with those with T/non-T hetero or T/T homo. There are G/G, G/A, G/C, A/A, A/C, and C/C as combinations of non-T/non-T homo. Combinations of T/non-T include T/G, T/A, and T/C.

Therefore, validity of interferon therapy for an HCV-infected patient can be detected prior to implementation of interferon therapy, for example by determining the nucleotide of the SNP site in ISRE of the polynucleotide which contains promoter regions of human MxA gene possessed by HCV-infected patient.

Based upon the discovery described above, according to the present invention, polynucleotides for detecting validity of interferon therapy are provided. In addition, a method for predicting whether interferon therapy is valid or not for the individual requiring interferon therapy is provided. Also provided is use of polynucleotides of the present invention as probes for detecting which SNP site the individual has.

Further, the present invention provides gene therapy for rendering an interferon-insensitive individual to be interferon-sensitive.

Still further, non-human transgenic animals harboring the nucleotides, which are useful as experimental animals, are provided.

Each aspect of the present invention is separately explained below.

Polynucleotide for Prediction of Validity of Interferon Therapy

In the present specification, "polynucleotide" means chemical substances formed by coupling two or more nucleosides through phosphate bonds. "Nucleosides" include, but not limited to, deoxyribonucleosides and ribonucleosides. Furthermore, peptide nucleic acid (PNA), morpholino nucleic acid and S-oligo nucleic acid are also referred to the "polynucleotide" in the present specification.

It should be noted that in the present specification, "promoter region" indicates not only the region directly involved in transcription initiation reaction such as TATA box, but also sequences including control sequences that exist in close proximity of or distant from said region to influence the efficiency of the transcription initiation reaction. Therefore, it should be noted that the term "promoter region" includes a sequence involved in the transcription initiation reaction alone, a control sequence alone, and a coupled sequence between the both sequences.

Incidentally, "ISRE" means a nucleotide sequence consisting of about 12 to 15 nucleotides which exist in the transcription control region of the gene induced by the stimulus of interferon $\alpha$, $\beta$, $\gamma$, or $\omega$.

The nucleotides of the present invention can include at least any one of following (a) to (e).

(a) Polynucleotide indicated by any one of Sequence ID Nos. 1, 2, 3, or 4.

(b) A modified polynucleotide derived from the polynucleotide listed in (a) by including one or several deletions, substitutions or additions at any positions except for 455th position.

Examples of the deletion, substitution and addition include deletion at 128th, 133rd, 152nd, 508th, and 543rd position, substitution at 330th position (G→T), and addition at 501st position Furthermore, also included in the polynucleotide of the invention are a combined polynucleotide in which the polynucleotide of the Sequence ID Nos. 1, 2, 3, or 4 or fragments thereof is coupled with at least one functional polynucleotide selected from the group consisting of a promoter, an enhancer, an upstream activation sequence, a silencers, a upstream suppression sequence, an attenuator, a poly A tail, a nucleus transport signal, Kozak sequence, ISRE, a drug resistance factor, a gene of signal peptide, a gene of transmembrane domein, a gene of marker protein (including luciferin gene, a green fluorescent protein gene, a phycocianin gene, a horseradish peroxidase gene), a gene of interferon-responding protein, and a gene of interferon-non-responding protein.

Still further, in the nucleotide sequences of said polynucleotides of Sequence ID Nos. 1, 2, 3, and 4, only one nucleotide at the SNP site (located at 455th position) is involved in the validity of interferon therapy. Therefore, the polynucleotide of the present invention can be a fragment of said polynucleotide containing the SNP site of said 455th position. The polynucleotide is preferably of length not shorter than 11 nucleotides and no longer than 30 nucleotides. More preferably, it is of length not shorter than 15 nucleotides. When the polynucleotide is too long, it is difficult to identify difference of one nucleotide. On the other hand, when the polynucleotide is too short, it is difficult to hybridize with and determine the nucleotide sequence of the polynucleotide included in the sample.

Particularly a polynucleotide of the present invention can be:

(c) A fragment of the polynucleotide of Sequence ID Nos. 1, 2, 3, or 4 including the 455th SNP site, a fragment containing the polynucleotide of Sequence ID Nos. 5, 6, 7, or 8 (namely said ISRE) corresponding to the sequence from 441st to 456th position of Sequence (d) A fragment of the polynucleotide of Sequence ID Nos. 1, 2, 3, or 4 including said 455th SNP site, the fragment containing the polynucleotide of Sequence ID Nos. 9, 10, 11, or 12 corresponding to the sequence from 449th to 459th position of Sequence ID Nos. 1, 2, 3, or 4. Particularly, since the fragment (d) has said SNP site roughly at the center thereof and contains nucleotide sequences of equal length on both sides, high-precision determination of nucleotide sequence can be achieved. In order to carry out detection of still higher precision, a fragments including the polynucleotide corresponding to the sequence from 447th to 461st position of Sequence ID Nos. 1 to 4 are preferable.

Further, a preferable polynucleotide of the present invention can be:

(e) A complementary strand of polynucleotide selected from the group consisting of (a), (b), (c) and (d).

Note that complementary strands of the polynucleotides indicated by Sequence ID Nos. 5, 6, 7, and 8 (i.e., the ISRE) are the polynucleotide strands of Sequence ID Nos. 13, 14, 15, and 16, respectively.

Note that complementary strands of the polynucleotide indicated by Sequence ID Nos. 9, 10, 11, and 12 are the polynucleotide strands of Sequence ID Nos. 17, 18, 19, and 20, respectively.

Method of Predicting Whether Interferon Therapy is Valid or Not

According to the present invention, by determining the nucleotide at the SNP site of an HCV-infected patient prior to the application of interferon therapy, it is possible to predict whether interferon therapy is valid to the HCV-infected patient. Since prediction as to whether interferon therapy is valid for a certain individual has previously been impossible, it is quite meaningful that such prediction has become possible by the embodiment of the present invention.

Therefore, the present invention provides a method for predicting whether interferon therapy is valid or not for an HCV-infected individual requiring the interferon therapy, which comprises:
1) taking a sample containing a polynucleotide which includes at least one interferon-stimulated response element; and
2) determining nucleotide located at the 2nd position from the 3' end of said at least one interferon-stimulated response element.
3) predicting that interferon therapy is valid for said individual if said nucleotide is thymine.

Also provided by the present invention is the method described above, which comprises, in place of the step 3), a step of predicting that interferon is highly possibly invalid for said individual when said nucleotide is guanine, adenine, or cytosine.

Further, since indicated diseases of interferon therapy are not limited by hepatitis C, the present invention provides a method of predicting whether interferon is valid or not for an individual requiring interferon administration, which comprises:
1) taking a sample containing a polynucleotide which includes at least one interferon-stimulated response element; and
2) determining nucleotide located at the 2nd position from the 3' end of said at least one interferon-stimulated response element.
3) predicting that interferon therapy is valid for said individual when said nucleotide is thymine.

Also provided by the present invention is the method described above, which comprises, in place of the step 3), a step of predicting that interferon is highly possibly invalid for said individual when said nucleotide is guanine, adenine, or cytosine.

An individual for whom the present invention should be applied can be the patient suffered from diseases for which interferon therapy, preferably interferon α, β or ω, is valid. Said individual can also be healthy people. Diseases for which interferon α, β, or ω is valid include, besides hepatitis C, glioblastoma, medulloblastoma, astrocytoma, malignant melanoma of the skin, hepatitis B, renal carcinoma, multiple myeloma, hairy cell leukemia, chronic myeloid leukemia, subacute screlosing panencephalitis, viral encephalitis, systemic herpes zoster and varicella of immunologic inhibition patients, undifferentiated epiphoryngeal carcinoma, viral internal ear infection disease accompanying hearing ability degradation, herpes corneae, flat condyloma, conjunctivitis due to adenovirus and herpesvirus, herpes progenitalis, herpes labialis, carcinoma uterine cervix, hepatic hydrothorax, keratoacanthoma, basal cell carcinoma, and delta chronic active hepatitis, but are not limited by them.

In order to carry out the method of the present invention, a sample containing a polynucleotide including interferon-stimulated response element is taken from an individual. The individual can be an arbitrary mammal including a human, a dog, a cat, a cow, a goat, a pig, a sheep, and a monkey, a human being the most preferable.

The "polynucleotide including interferon-stimulated response element" can be, but not limited to, the polynucleotide which include control sequences (promoter regions, etc.) located upstream of the gene encoding interferon-stimulated response proteins. The "polynucleotide including interferon-stimulated response element" is preferably the polynucleotide of sequence Nos. 1 to 4, or a fragment of said polynucleotide including the sequence from 441st to 456th position thereof.

Since polynuicleotides are widely distributed in a body, any arbitrary sample taken from an individual can be the "sample containing polynucleotide which includes interferon-stimulated response element". A preferable sample is blood.

After taking the sample from the individual, operations of extracting polynucleotides from the sample are generally carried out. For example, phenol extraction, ethanol precipitation, or other arbitrary methods of extraction can be used for extracting polynucleotides from biological components. When m RNA is extracted, oligo dT column can be used.

When the amounts of the polynucleotides are small, the polynucleotides can be amplified as required. The amplification can be carried out by means of polymerase chain reaction (to be abbreviated as PCR hereafter) including reverse transcription polymerase chain reaction.

After carrying out extraction and/or amplification, if required, the nucleotide at the SNP site located at the 2nd position from the 3' end of at least one interferon-stimulated response element is determined.

In order to determine the nucleotide at the SNP site, most generally, interferon-stimulated response element can be sequenced. The sequencing may be performed after the interferon-stimulated response element is amplified using a pair of primers which sandwich the interferon-stimulated response element including the nucleotide to be determined, or without the amplification.

The restriction fragment length polymorphism (RFLP) method can be used when the nucleotide to be determined is located in the recognition site of the restriction endonuclease. For example, in case of the promoter region of the MxA gene, while the ISRE of sequence No. 3 having guanine at the 455th position is cleaved by the restriction endonuclease HhaI capable of specifically recognizing and cleaving the base sequence GCGC, it is not cleaved when the 455th nucleotide is not guanine. Therefore, the RFLP method using HhaI can be used in the case of identifying the 455th nucleotide of sequence No. 1.

As other methods for identifying polymorphism, it is possible to use known methods including, but not limited to, the PCR-SSP (PCR-specific sequence primers) method, the PCR-SSO (PCR-sequence specific oligonucleotide) method that is a combination of the dot blot method and PCR, and the PCR-SSCP.

It should be noted that the dot blot method is one of the methods for detecting nucleic acid strands of specific sequences in samples, by using probe nucleic acids with known sequences. In this method, a sample of single stranded nucleic acid is immobilized on the organic film disposed on the substrate, and then a solution of a single-stranded probe polynucleotide labeled with fluorescent marker, etc. is contacted with the sample on a thin film. If the sample has a sequence complementary to the probe polynucleotide, the probe hybridizes with the sample nucleic acid to form a double strand to be immobilized on the substrate. Therefore, the sample nucleic acid complementary to the probe can be detected by detecting the marker labeled to the probe after removal of nonreacted nucleic acid by washing. Thus, the present invention also includes the use of the polynucleotide of the present invention as the probe, in detecting genetic polymorphism of MxA proteins. Further, the test reagents for predicting whether interferon therapy is valid or not for an individual to be administered with interferon, which comprises a polynucleotide of any one of Sequence No. 1 to No. 4 are also included in the present invention.

The methods described above can identify the nucleotide at the SNP site located at the second from the 3' end of the interferon-stimulated response element, and predict that interferon therapy is valid when the nucleotide is thymine. Alternatively, when said nucleotide is guanine, adenine, or cytosine, interferon therapy can be predicted as highly probably invalid for said individual.

Gene Therapy

As mentioned above, in order for interferon therapy to be valid to an individual, the individual need to possess a polynucleotide selected from the group consisting of the following:

(at) the polynucleotide of Sequence ID No. 1 in the sequence listing shown later;
(bt) a modified polynucleotide derived from the polynucleotide (at) by including one or several deletions, substitutions or additions at any positions except for 455th position;
(ct) a polynucleotide containing the sequence which spans from 441st to 455th position of Sequence ID No. 1;
(dt) a polynucleotide containing the sequence which spans from 449th to 459th position of Sequence ID No. 1; and
(et) a complementary strand of polynucleotide selected from the group consisting of (at), (bt), (ct) and (dt).

Therefore, the nucleotides (at) to (et) described above can be used in gene therapy for making interferon valid, wherein an interferon-insensitive individual is rendered to be interferon-sensitive, by introducing polynucleotide of the present invention into an interferon-insensitive individual.

In other words, the present invention includes a method for rendering an interferon-insensitive individual to be interferon-sensitive, which comprises introducing at least one polynucleotide selected from (at) to (et) described above into an interferon-insensitive individual. Also included in the present invention is a vector for rendering an interferon-insensitive individual to be interferon-sensitive, comprising at least one polynucleotide selected from (at) to (et) described above. Further, the present invention includes use of at least one polynucleotide selected from (at) to (et) described above in manufacture of pharmaceuticals for rendering an interferon-insensitive individual to be interferon-sensitive.

Moreover, the vectors of the present invention described above can also be used for producing proteins that can confer interferon-sensitivity to a mammal, by transforming an appropriate host with the vector and expressing them.

Transgenic Animals

Non-human transgenic animals can be prepared by the method known to the art, using the polynucleotides of the present invention. The non-human transgenic animals are useful as test animals for the research of functions of interferon.

EXAMPLE 1

In this example, it has been proved that HCV patients having a homozygous or heterozygous MxA gene which has thymine at 88th position (corresponding to 455th position in the nucleotide sequence of Sequence ID No. 1) in the promoter region (to be described MXA(T) hereafter) exhibit better response to interferon therapy than HCV patients having homozygous MxA gene which has guanine at that position (to be described as MxA(G) hereafter).

Subject 115 patients histologically proved to be suffered from chronic hepatitis C and receiving interferon therapy and 42 healthy persons with anti-HCV antibody negative took part in this study. All of them are Japanese and do not have blood relationship with each other.

Among the 115 patients, 52 were in the normal level of serum alanine aminotransferase during follow-up term of at least 6 months after completion of interferon therapy, and were sustained responders (to be described as NR hereafter) with HCV RNA always negative, and 63 patients were remained HCV RNA positive during the follow-up term independent on the ALT level, or non-responders with relapsed hepatitis C (to be called NR hereafter). Total dose of over 300 million units of interferon $\alpha$ and/or $\beta$ were administered to all the patients.

MxA Gene Analysis

Nucleic acids were extracted from the BPMC sampled from the patients and the healthy controls. Said nucleic acids were subjected to PCR to amplify DNA having 599 nucleotides which contains the promoter region of MxA genes.

The outline of PCR was as follows.

After mixing 0.05 $\mu$g of nucleic acid with Taq-Gold (Perkin-Elmer), oligonucleotide primer #MXAF01 of Sequence ID No. 12 (forward primer, 569th to 540th site), and oligonucleotide primer #MXAF02 of Sequence ID No. 6 (reverse primer, 30th to 1st site), reaction was carried out under the cycle condition of [95° C./10 minutes], [95° C./10 seconds, 68° C./60 seconds]×55, [72° C./7 minutes]. By the direct sequencing of the PCR products, sequences of 12 samples out of 157 were determined.

After identification of the SNP sites in the amplified regions by sequencing, RFLP systems for the detection of nucleotides of alleles in a distinguishable manner was established. PCR products of the 599th nucleotides from all the patients were digested with HhaI(GCG↓C), and if either one or both of a 482 nucleotides-band and a 533-nucleotides band are formed or not was examined by electrophoresis in an agarose gel.

Statistical Analysis

Group data were compared by Fischer's precise probability test with or without Yate's correction. p<0.05 was regarded as statistically significant.

Result

From sequencing of 12 samples, SNP sites in the promoter region of MxA genes are identified. SNP (G and T) existed at the 88th site of said promotor region, said SNP being contained in the regions similar to ISRE shown in FIG. 1 (SEQ ID NO:23).

In the RFLP by HhaI that followed, gene types of MxA genes from all the 157 samples are determined. In this assay, samples having guanine at the SNP sites showed a band of 482 base pairs in the electrophoresis gel. On the other hand, when guanine is replaced by thymine, a band of 533 base pairs appeared because the restriction site recognized by HhaI disappeared. In case of heterozygote in which the promoter region having guanine at the SNP site and the promoter region having thymine at the SNP site, both the bands of 482 and 533 base pairs are detected (see FIG. 2).

As shown in Table 1, 62% of the patients in the NR group owned the homozygous promoter region having guanine at the SNP site (G.G Homo), while 33% of the patients in the SR group were G.G Homo (p=0.0009; SR vs.NR). On the contrary, 35% of the patients in the NR group were heterozygous who possess promoter region having guanine at the SNP site and the promoter region having thymine at the SNP site (G.T Hetero), while 60% of the patients in the SR group were G.T Hetero (p=0.0082; SR vs.NR). Patients of T.T Homo were 3.2% in the NR group and 10% in the SR group respectively (p=0.0018; SR; vs.NR).

While the frequency of alleles having promoter regions in which the SNP site is guanine was 0.606 in the SR group, it was 0.794 in the NR group (p=0.0018; SR vs.NR).

TABLE 1

| Polymorphism at −88th Site if MxA promoter | SR patient (n = 52) | NR (n = 63) | Healthy Control (n = 42) | P: SR vs NR |
|---|---|---|---|---|
| Allelic frequency | | | | |
| G | 0.606 | 0.794 | 0.714 | 0.0018 |
| T | 0.394 | 0.296 | 0.286 | 0.0018 |
| Zygote type | | | | |
| G · G Homo | 16(31%) | 39(62%) | 20(48%) | 0.0009 |
| G · T Hetero | 31(60%) | 22(35%) | 20(48%) | 0.0082 |
| T · T Homo | 5(10%) | 2(3.2%) | 2(4.8%) | 0.2956* |

*Yate's revision was implemented

Further the above result that individuals with G.G Homo are significantly fewer in the SR group than in the NR group was made clear to be independent of the gene types of HCV the patients were infected.

TABLE 2

| Zygote type of SNP Located at −88th site of MxA promoter | SR patient | NR patient | p: SR vs NR |
|---|---|---|---|
| Patient infected by HCV of Gene of 1b type | n = 18 | n = 42 | |
| G · G Homo | 5(28%) | 26(62%) | 0.0321* |
| G · T Hetero | 12(67%) | 14(33%) | 0.0170 |
| T · T Homo | 1(5.6%) | 2(4.8%) | 0.6051* |
| Patient infected by HCV of Gene of 2a or 2b type | n = 34 | n = 21 | |
| G · G Homo | 11(32%) | 13(62%) | 0.0318 |
| G · T Hetero | 19(56%) | 8(38%) | 0.1999 |
| T · T Homo | 4(12%) | 0 | 0.2722* |

*Yate's revision was implemented

It is apparent from Table 2 that in both of the patient group infected with HCV (HCV 1b group) of 1b gene type and the patient group infected with HCV (HCV 2a/2b group) of 2a or 2b gene type, 62% were G.G Homo individuals in the NR group, while 28% and 32% were G.G Homo individuals in the SR group. The result shown in Table 2 revealed that G.G Homo individuals are significantly fewer in the SR group independent of the gene type of HCV the patients were infected (HCV 1b group; p=0.0321, HCV 2a/2b group; p=0.0318).

In summary, the present example proved that HCV-infected patients possessing homozygous or heterozygous MxA ptomoter region which has thymine at the SNP site are more highly responsible to interferon therapy independent on the gene type of the infected HCV.

Further, the present example also suggests that HCV-infected patients having homozygous or heterozygous MxA ptomoter regions which has not guanine at the SNP site is highly responsible to interferon therapy.

Further, these finding may be applicable to diseases other than hepatitis C, since said SNP site exists in ISRE.

EXAMPLE 2

As made clear in Example 1, treatment of hepatitis by interferon administration is highly effective with HCV-infected patients whose SNP of the MxA promoter is T type. On the other hand, in case the SNP is G type, the treatment is less effective. These facts are construed as follow: while the T type of nucleotide sequence of ISRE correctly responds to the stimulus of interferon to achieve sufficient production of MXA proteins, the G type with one base different from the sequence does not respond to the stimulus of interferon resulting in less production of MxA proteins.

From this point of view of the situation, interferon therapy is also assumed to be less effective in HCV hepatitis patients having C and A types of SNP of MxA promoter, since the MXA promoters do not respond to interferon as in the case of G type.

In order to prove them, a plasmid having luciferase gene downstream of the MxA promoter was constructed and was transfected into human cells (HeLa cells and ovary cancer cells). Then, the activities of luciferase produced as the result of the response of the MXA promoter to interferon were examined in each case of MXA promoters having any one of 4 kinds of SNPs (T, G, A, and C types).

Figure 3:
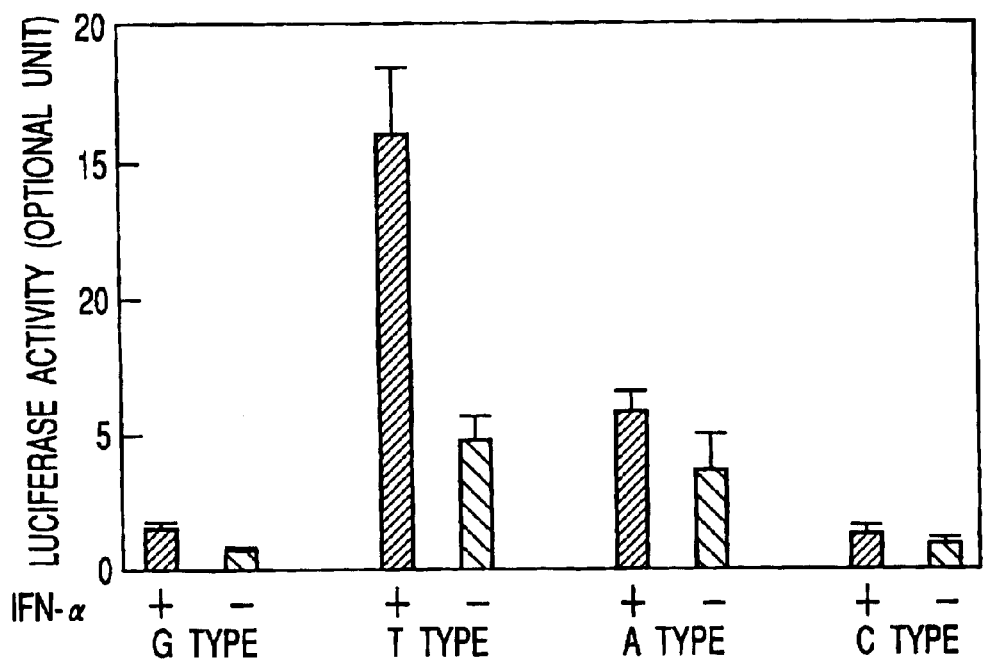
FIGS. 3, 4, 5 and 6 are graphs showing comparison of responsibility to interferon α and β among MxA promoters having four kinds of SNP (T type, G type, A type and C type). The results were obtained in Hela cells and ovarian cancer cells by using, as an indicator, luciferase activity under the control of said promoters.
Figure 4:
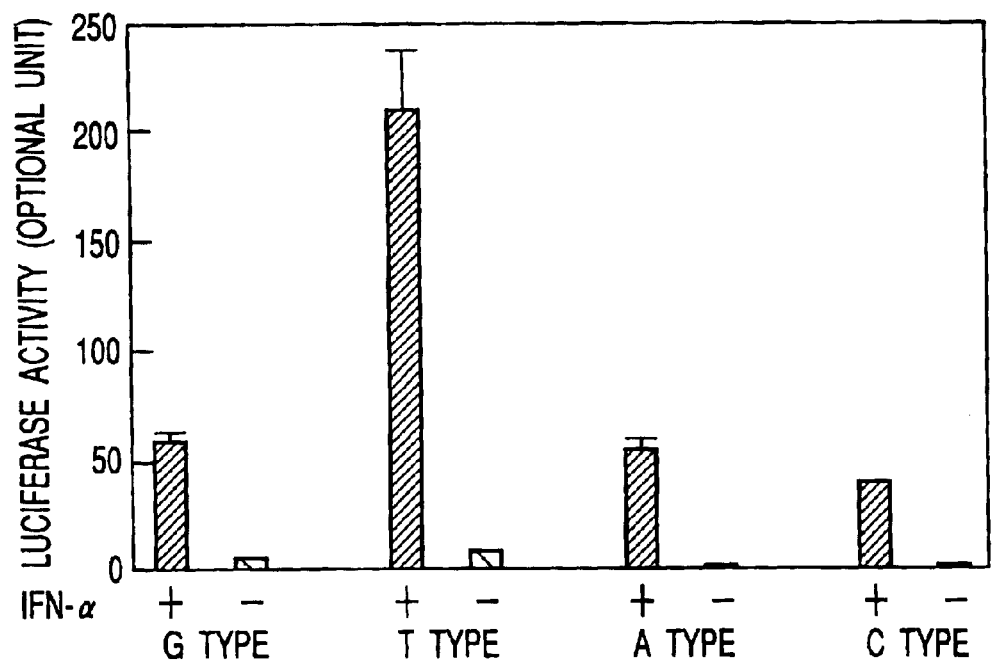
Figure 5:
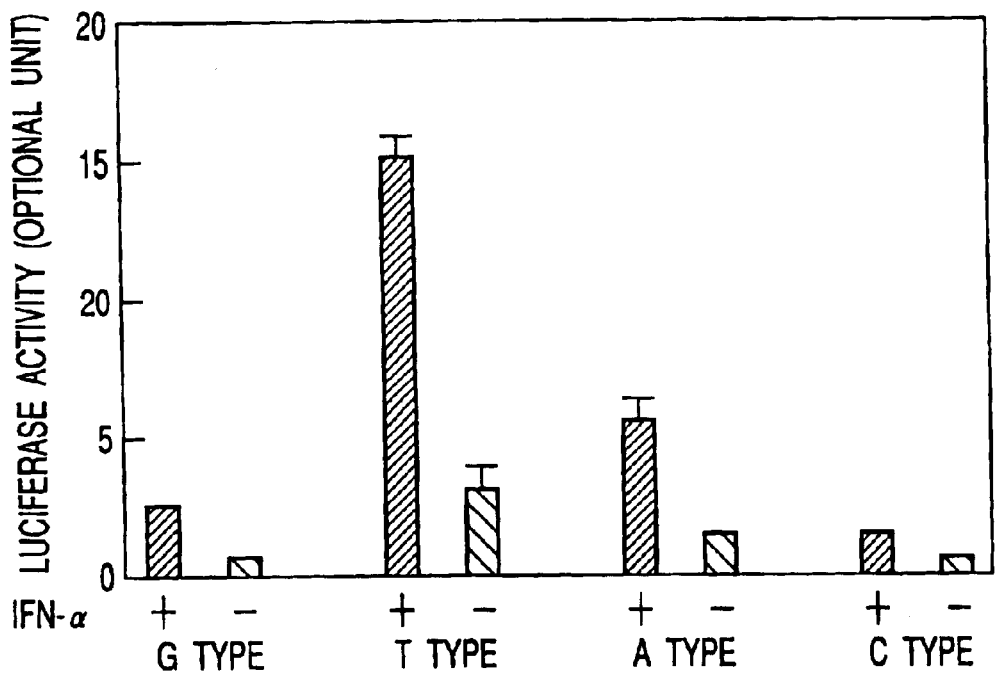
Figure 6:
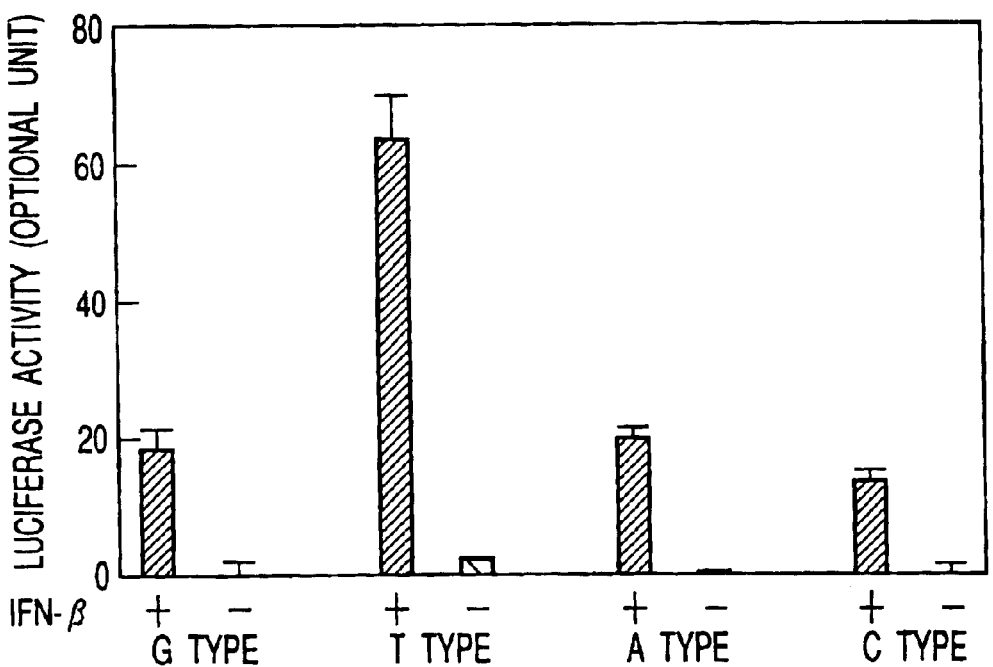

The results are shown in FIGS. 3 to 6. FIG. 3 is the example of induction in Hela cells using interferon α, FIG. 4 is the example of induction in ovary cancer cells using interferon α, FIG. 5 is the example of induction in Hela cells using interferon β, and FIG. 6 is the example of induction in ovary cancer cells using interferon α. In these figures, + indicates luciferase activity when interferon was added, and − indicates luciferase activity when interferon was not added. All the results are mean values of three experiments, and standard deviations are displayed using bars.

It is apparent from the figures that T type MxA promoter shows the highest values in all the cases. On the other hand, the response of HCV hepatitis patients having SNP of A and C types to interferon α and interferon β is low as in the case of G type, and thus, effect of the interferon therapy is predicted to be low.

EXAMPLE 3

In this example, formation of MxA proteins in an embryonic stem cells (to be described as ES hereafter) introduced with MxA genes is described.

In the PCR method, primers #MXAF01 (Sequence No. 5) and #MXAR02 (Sequence No. 6) were used to amplify the region containing the MxA genes which has T (MxA(T)) and G (MxA(G)) at the −88th position of promoter regions. Next, ES cells were transfected with the amplified products by the calcium phosphate method. Reaction conditions reported earlier were followed for all the reactions. These cells were subjected to the action of INF-α and the amount of production of the MxA proteins were compared by Norhtern blotting.

As a result, it is confirmed that the amount of MxA protein produced in the cells transfected with MxA(G) genes were as much as 1.2 times in comparison with control cells not transfected with MxA(G) genes. On the other hand, the cells transfected with MxA(T) genes were found to produce MxA proteins about 2.5 times as much as in the control cells and about twice as much as in the cells transfected with MxA(G) genes.

This example showed that much MxA proteins can be produced by introducing MxA(T) genes to ES cells.

The result of this example suggested the possibility of gene treatment for the diseases to which interferon is effective, by using ES cells to which MxA genes are introduced.

Also chimeric animals can be made utilizing the ES cells transfected with the MxA genes. Further, transgenic animals can be generated by the cross fertilization of the chimeric animals.

EXAMPLE 4
Introduction of Genes to ES Cells

MxA genes were introduced by electroporation to ES cells after being cultured in an ES/LIF culture medium. The condition of electroporation is shown below.

Composition of the solution: 20 mmol/L-HEPES (pH 7.3), 137 mmlo/L-NaCl, 5 mmlo/L-KCl, 0.7 mmol/L-Na$_2$HPO$_4$, 6 mmol/L-glucose, 0.1 mmol/L-2-mercaptoethanol Conditions: 450 v, 250 μF, 10 min., room temperature, 4 mm cuvette.

After electroporation, the cells were transferred to the ES/LIF culture medium, and the cells having the introduced genes were selected as reported earlier using 200 μg/L of aminoglycoside phosphotransferase (G418) and 2 μmlo/L of ganciclovir (GANC). DNA was extracted from the cells obtained, and the objective fragments were confirmed by Southern hybridization to have been introduced.

This example showed that genes can be introduced to ES cells by electroporation.

EXAMPLE 5

Figure 7:
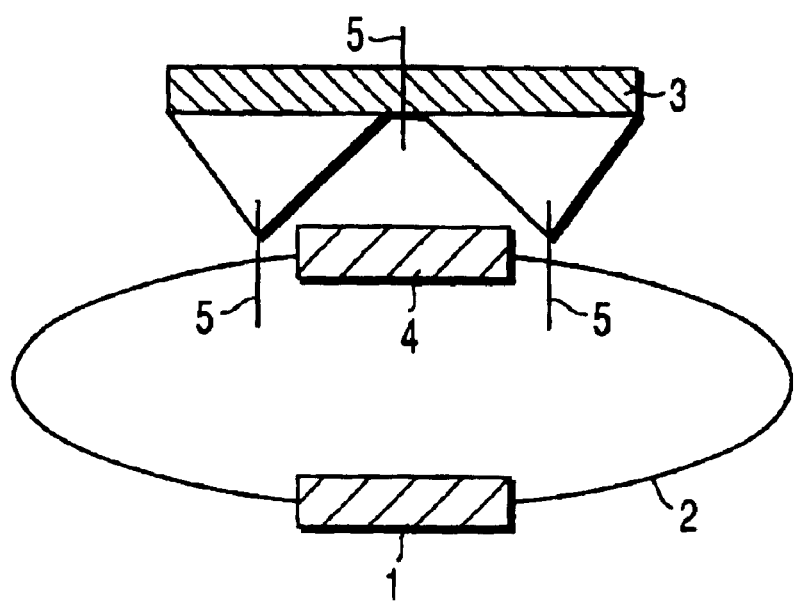
FIG. 7 schematically shows the structure of the Ptnk vector in which a gene is introduced.

In this example, incorporation of MxA genes into vectors is explained.

primers #MXAF01 (Sequence No. 5) and #MXAR02 (Sequence No. 6) were used to amplify the region containing the MxA genes which has T (MxA(T)) and G (MxA(G)) at the −88th position of promoter regions. Next, the amplified product was incorporated into the PNTK vector (FIG. 7) according to the routine methods well known to the art.

Reaction conditions reported earlier were followed for all the reactions. The vector was cleaved to straight using a restriction endonuclease, and then used for incorporating the gene.

The vector in which MxA genes were incorporated can be used to introduce MxA genes into the objective cells, thereby improving responsibility to interferon.

EXAMPLE 6

In this example, production of MxA proteins in the ES cells transfected with MxA genes is explained.

Those cells transfected with MxA(T) or MxA(G)genes were subjected to the action of INF-α, and the amounts of production of MxA proteins were compared. As the result of comparison by Northern blotting, production of about 1.5 times as much MxA proteins was confirmed in the cells transfected with the MxA(G) gene, in comparison with the control cells not subjected to any action. On the other hand, it was found that the cells transfected with MxA(T) gene showed the value amounting to about 4.5 times as much as in the control cells and about 3 times as much as in the cells transfected with MxA(G).

The results described above suggested the possibility that gene therapy for diseases in which interferon is effective can be carried out by using the ES cells transfected with MxA genes.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A polynucleotide comprising the polynucleotide of SEQ ID NO:1 (at), or comprising the complementary strand of the polynucleotide of SEQ ID NO:1.

2. The polynucleotide of claim 1, which comprises the polynucleotide of SEQ ID NO:1 (at).

3. The polynucleotide of claim 1, which comprises the complementary strand of the polynucleotide of SEQ ID NO:1.

4. The polynucleotide of claim 1, further comprising at least one additional polynucleotide connected to said polynucleotide, the additional polynucleotide being selected from the group consisting of a promoter, an enhancer, an upstream activation sequence, a silencers, a upstream suppression sequence, an attenuator, a poly A tail, a nucleus transport signal, a Kozak sequence, an ISRE, a drug resistance factor, a gene of signal peptide, a gene of transmembrane domain, a gene of marker protein, a gene of interferon-responding protein, and a gene of interferon-non-responding protein.

5. A vector comprising the polynucleotide of claim 1.

6. The polynucleotide of claim 2, which is suitable for predicting the efficacy of interferon therapy using interferon-α and/or interferon-β for treating an individual who suffers from hepatitis C virus.

7. The polynucleotide of claim 3, which is suitable for predicting the efficacy of interferon therapy using interferon-α and/or interferon-β for treating an individual who suffers from hepatitis C virus.

8. A vector comprising the polynucleotide of claim 2.

9. A vector comprising the polynucleotide of claim 3.

* * * * *